US005359997A

United States Patent [19]

Rigo et al.

[11] Patent Number: 5,359,997

[45] Date of Patent: Nov. 1, 1994

[54] APPARATUS FOR CONTROLLABLY TREATING HAIR BY TEMPERATURE AND TIME USING A NEBULIZED MIXTURE OF AIR, STEAM AND OZONE

[76] Inventors: Giuseppe Rigo, C.so Europa 675/7; Enzo Bertolacci, Via Emilio Salgari 209/20, both of Genova, Italy

[21] Appl. No.: 858,051

[22] Filed: Mar. 26, 1992

[30] Foreign Application Priority Data

Mar. 29, 1991 [IT] Italy ........................ GE91 A 000054

[51] Int. Cl.$^5$ .............................................. A61M 15/00

[52] U.S. Cl. ............................ 128/202.16; 128/202.25

[58] Field of Search ....................... 128/202.25, 203.12, 128/202.16, 202.17, 203.25, 203.26, 202.26; 4/524, 535, 537; 34/97, 99, 100

[56] References Cited

U.S. PATENT DOCUMENTS

| | | | |
|---|---|---|---|
| 481,676 | 8/1892 | Sharp | 128/202.25 |
| 912,742 | 2/1909 | Shute | 128/202.26 |
| 1,965,424 | 7/1934 | Mascolo | 128/203.26 |
| 2,292,666 | 8/1942 | Schurtz | 4/537 |
| 2,415,659 | 2/1947 | Steel | 128/202.25 |
| 2,566,531 | 9/1951 | Nissenbaum | 4/537 |
| 3,194,236 | 7/1965 | Wehner | 128/202.25 |
| 3,232,292 | 2/1966 | Schaefer | 128/202.25 |
| 4,205,692 | 6/1980 | Losenno | 4/537 |
| 4,553,339 | 11/1985 | Rigo | 34/99 |
| 4,766,913 | 8/1988 | Klein | 34/99 |
| 4,932,400 | 6/1990 | Persinger | 128/202.25 |
| 5,052,382 | 10/1991 | Wainwright | 128/202.25 |

*Primary Examiner*—Edgar S. Burr
*Assistant Examiner*—Aaron J. Lewis
*Attorney, Agent, or Firm*—Notaro & Michalos

[57] ABSTRACT

Apparatus for trichotechnical and aesthetic hair treatments based on the use of a nebulized mixture of air, steam and ozone, which apparatus comprises suitable means for enabling the amount of each component of the mixture, as well as the mixture application temperature—with the latter being anyway designed to be controlled at values similar to, or lower than, user's body temperature—to be independently, either manually or automatically, controlled, securing the obtainment of optimal temperature values and distribution pattern of the treatment mixture inside a bell-shaped headpiece, as well as a controllable ozone production, thanks to the use of electric-brush discharge ozone generators (ozonizers), the magnetic field of which is completely dissipated without neutral conductive connection to earth by virtue of a specific shielding of the containers of the electric-brush generator bulbs with a brass net, with means being furthermore provided in order to feed the mixture into the headpiece, which means are suitable for maximizing the amount of treatment mixture available inside said headpiece, with the absorbed power by the boiler being the same, all the above with extremely short end application times, and securing a considerable energy saving.

8 Claims, 3 Drawing Sheets

APPARATUS FOR CONTROLLABLY TREATING HAIR BY TEMPERATURE AND TIME USING A NEBULIZED MIXTURE OF AIR, STEAM AND OZONE

FIELD AND BACKGROUND OF THE INVENTION

The present invention relates to an apparatus for aesthetical-trichotechnical treatments based on the use of a nebulized mixture of air, steam and ozone, at a temperature lower than, or similar to, a user's body temperature.

Apparatuses of similar types have been known, which generate steam and ozone, gas substances, by means of a forced air jet through ducts to a bell-shaped headpiece, into which the user's head is inserted in order to undergo the suitable treatment.

The drawbacks which have always affected these apparatuses are caused, first of all, by the presence of high temperatures—which may reach, or even exceed, 60° C.—and large amounts of steam inside the headpiece, because of the considerably large amounts of condensate which are produced inside said headpiece. Consequently, there are condensate disposal problems, due to the required long application times, the impossibility of controlling the temperature of the end treatment mixture, and the various levels (i.e., percentages) of the various substances which constitute said mixture, as well as the unevenness of temperature and vapourization volume in the various internal regions of the headpiece, with consequent differences in effectiveness on the user's hair. Other drawbacks are caused by the low level of ozone in the mixture, when ozone is generated by lamps, or by the presence of intense magnetic fields when ozone is generated by generators.

SUMMARY OF THE INVENTION

The present invention overcomes the above listed drawbacks, thus substantially enabling the application to be carried out onto a user's hair. The present invention uses a mixture with an either manually or automatically controllable temperature starting from values of 28° C. through a nebulizing air jet, in which, the steam which entrains the molecules of the active principle used, and ozone, can be varied as desired, with said mixture being nebulized in a differentiated way into the interior of the headpiece, so as to compensate for the different temperatures of the various cutaneous region which drastically decreases the treatment times. The present invention allows for the production of extremely low amounts of condensate, which are subsequently disposed of, and uses a "time" parameter—like all other concerned parameters—which is controllable as desired by the operator, both by means of manual operations and according to automatic schedule programs, due to a central control panel installed onto the chassis of the apparatus.

The apparatus according to the present invention makes it possible for the above listed advantages to be achieved due to the use of the following means listed below.

The present invention uses a steam generating boiler with a supplementary filling/replenishment tank and level-regulation float, equipped with at least one heating metal-clad resistor and a temperature-monitoring thermostat. Ozonized, compressed air is fed into the boiler.

A first double-outlet solenoid valve for steam intake from the boiler is also used. The valve can be actuated either manually or automatically, in order to control the amount of steam to be fed to the headpiece and, if necessary, in order to totally close a steam outlet leading to the main channel. The steam outlet is suitable for sending steam to the headpiece through an alternate duct leading through a condensate-collecting tank which causes a sharp decrease in the steam temperature and, consequently, of the temperature inside of the interior of the headpiece.

The condensate collecting tank is equipped with a discharge outlet with a stop cock, i.e. a condensate inlet, and is connected with the steam outlet valve so that the steam is caused to bubble through the condensate collected in said tank, before reaching the headpiece, through a double-function duct which also performs the task of conveying to said tank the condensate produced inside said headpiece. The duct is connected with said headpiece through a "Y"-shaped fitting with two outlet openings and one inlet opening. The fitting is housed inside an inwards bend of the edge of the headpiece in the region of user's nape, i.e., the physically lowermost point of said headpiece.

The present invention also uses an ozonized air-steam mixing chamber, connected with the above-listed steam valve, as well as connected with a second solenoid valve which performs the task of controlling and/or intercepting the stream of ozonized air. The present invention is further provided with a primary recovery condensate tap connected with the boiler, and with a fitting for connection with a condensate collecting and drain chamber installed on the main duct which feeds the treatment mixture to the headpiece.

The condensate collecting and drain chamber installed on the main duct which feeds the treatment mixture to the headpiece is connected to the chamber by means of a suitable duct to a waste condensate collecting and steam cooling/purification tank.

A second, manually or automatically-controlled solenoid valve is used in order to regulate or discontinue the injection of ozonized air into the treatment mixture, with a second outlet suitable for conveying pressurized ozonized air to the boiler.

A non-return valve of the compressed,-ozonized air feed duct is used to feed the air to the above-listed valve. A double compressed-air ozone mixing chamber is also provided. At least one pair of ozone generators are used wherein respective bulbs are housed inside the mixing chambers. The chambers are wrapped inside a brass net with mesh openings smaller than 0.5 $mm^2$ and made from a brass wire with a cross-section surface-area comprised within the range of from 0.1 to 0.3 $mm^2$, which causes the absorption of the magnetic fields produced, without a conductive connection with earth being necessary.

The present invention uses a double membrane compressor capable of generating compressed air, destined to drive the treatment mixture.

A bell-shaped headpiece, made of poly(methyl methacrylate) or other suitable materials,-is also provided. The headpiece is electrically insulated from all components in which main voltage is used, without the usual openings for temperature drain, and has, in its interior, five ducts for treatment with a nebulization mixture, equipped with microbores. Four of these ducts run along a ring path, and the micro-bores, spaced apart 2–6 cm from each other, are orientated towards the interior of the headpiece and diagonally downwards—i.e., towards the internal wall of the headpiece, and not towards the user's scalp, thus inducing the formation of turbulences suitable for optimizing the distribution of the treatment mixture inside the headpiece. The different distances between said bores causes the internal temperature inside the headpiece to be controlled at different temperatures in different headpiece regions, complementarily to the temperature values of the user's skin regions.

A temperature-monitoring sensor is used and positioned in a position, which is determined by way of experiments, for determining the optimal position for detecting the average temperature value of the various internal headpiece regions, i.e., at the center of the innermost treatment mixture nebulization ring duct. Through the sensor, by means of a usual electrical three-relay system, it optimizes the several functions of the apparatus, controlling solenoid valves opening/closing, resistors switching on/off, feeding air/ozone amounts.

A control/check panel is also provided and is equipped, with a digital-display time counter, suitable for scheduling the necessary time for turning on/off the various circuits. The panel is also programmable for time values of minute fractions. A further digital display suitable for allowing the internal headpiece temperature to be programmed with the aid of the already cited temperature sensor is also provided.

BRIEF DESCRIPTION OF THE DRAWINGS

In order to better illustrate these, and further, features of the device according to the present invention, a preferred example of practical embodiment of the same invention is disclosed now by referring to the accompanying schematic drawings, in which.

DESCRIPTION OF THE PREFERRED EMBODIMENTS

Figure 1:
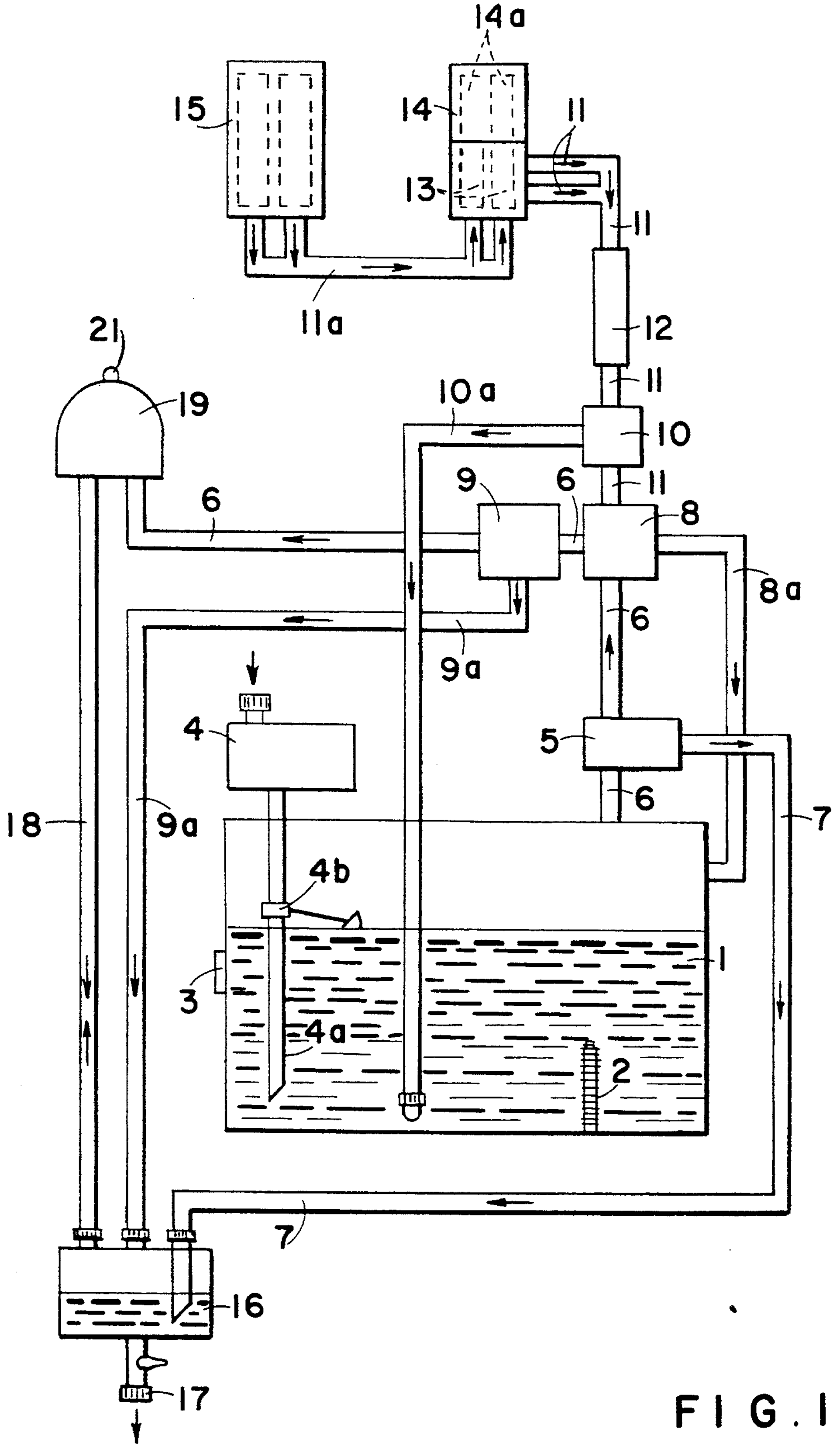
FIG. 1 is a schematic view of an apparatus according to the invention.

In the accompanying drawings, particularly FIG. 1, numeral 1 designates a steam production boiler, numeral 2 designates a metal-clad heating resistor, 2*a* designates a potentiometer for manual control of temperature, numeral 3 and 3*a* respectively designate a boiler temperature sensing thermometer and the temperature display on the control panel. Numerals 4, 4*a* and 4*b* respectively designate a supplementary boiler filling/replenishment tank, a water feed duct and a level-regulation float. Numeral 5 is a first, double-outlet solenoid valve for steam intake from the boiler 1, installed on a main duct 6 and through which a treatment mixture is fed to a bell-shaped headpiece 19. A second outlet of said valve 5 is connected with an alternate duct 7 through a waste condensate collecting tank 16 and a double-function duct 18.

Figure 2:
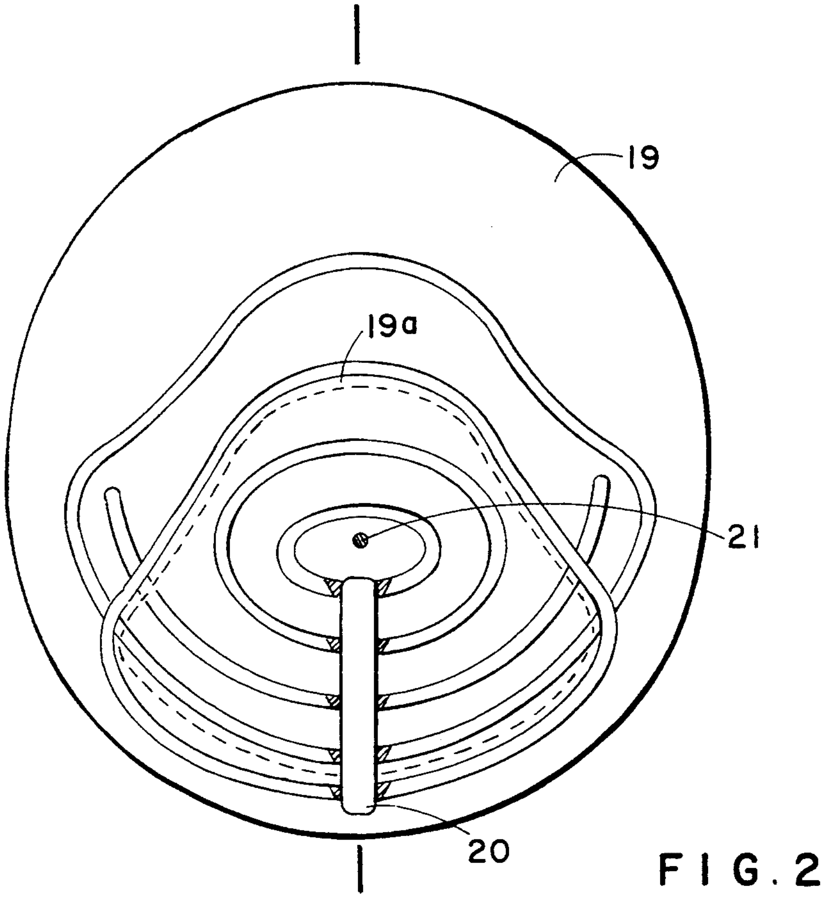
FIG. 2 is a perspective front elevation view of a bell-shaped headpiece according to the present invention.
Figure 3:
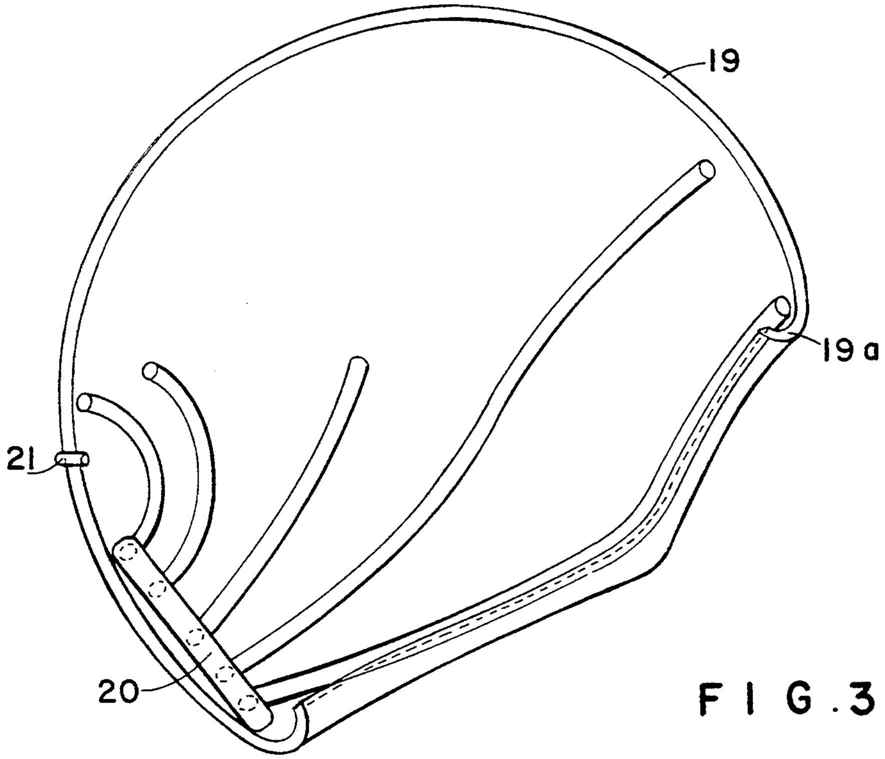
FIG. 3 is a sectional view of the headpiece of FIG. 2.

The duct 18 is connected with the headpiece 19 at the lowermost point of the headpiece 19, i.e. in the headpiece nape region. The headpiece edge is bent inwards, thus creating a condensate-collecting channel 19*a* (FIGS. 2 and 3). The condensate drawings along said duct 18, eventually reach the tank 16. When the valve 5 is commanded by a sensor 21 through an associated electrical system and having three relays, it discontinues the steam flow along a main duct 6. The steam stream which has reached the headpiece 19 through the duct 7, is cooled by the flowing (bubbling) through the condensate inside the tank 16, and is further cooled while flowing through the duct 18. This counter-current flow to the stream of condensate flowing from the condensate collecting channel 19*a* to the condensate collecting tank 16.

Along the main steam feed duct 6, there is installed a steam-ozonized air mixing chamber 8, with the condensate recovered in said chamber 8 being sent to the boiler 1 through the duct 8*a*, and a condensate discharge chamber 9, from which condensate is drained to the collecting tank 16 through the duct 9*a*.

The duct 11 is connected with the mixing chamber 8 so that the feed of compressed air mixed with ozone is provided immediately upstream of said chamber 8. The second solenoid valve 10 is provided on said duct 11, according to the present invention, which also performs the task of enabling ozonized air to be fed, through the duct 10*a*, to the boiler 1.

The formation of compressed air as mentioned above, takes place by means of the double compressor 15. Compressed air reaches the pair of mixing chambers 13 through the duct 11*a*, and inside which ozone is generated. From said mixing chambers 13, the duct 11 emerges, and reaches the valve 10, with the interposition of an intermediate non-return valve 12.

Figure 4:
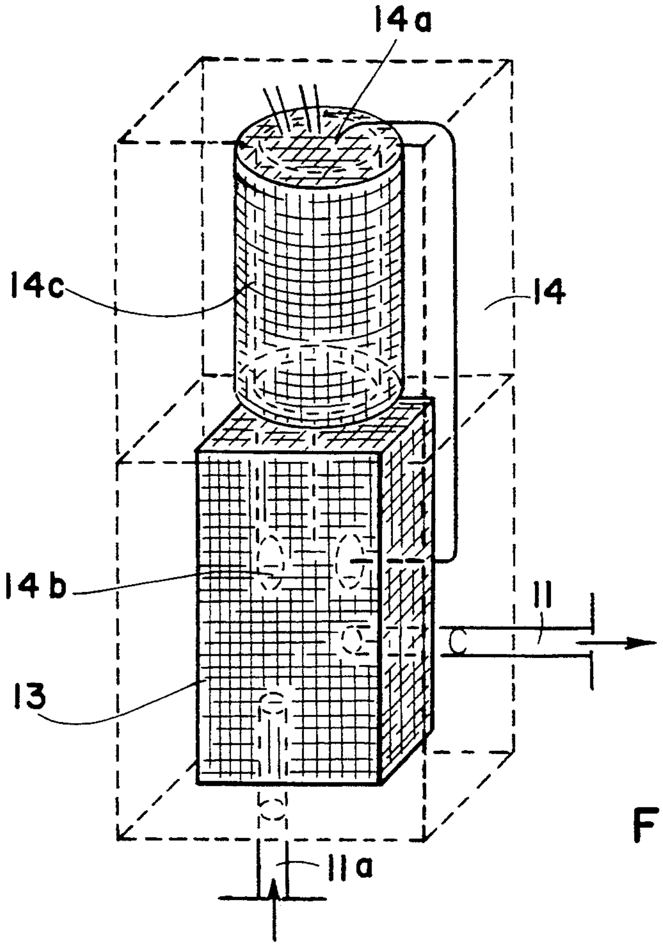
FIG. 4 is a schematic view of an ozone generator used with the present invention.

FIG. 4 shows bulbs 14*b* of the ozone generator 14 contained inside two tightly sealed plastic boxes, viz., mixing chambers 13, and that the latter are surrounded by a wrapped brass net 14*c* which also surrounds capacitors 14*a* for absorbing the magnetic field. The mesh openings are smaller than 0.5 $mm^2$ and made from a brass wire with a cross-section surface-area comprised within the range of from 0.1 to 0.3 $mm^2$. This allows for a strong magnetic field, as well as furthers arc discharge to be dissipated, both of which would be generated during the formation of the electrical discharge inside the bulbs 14*b*.

Figure 5:
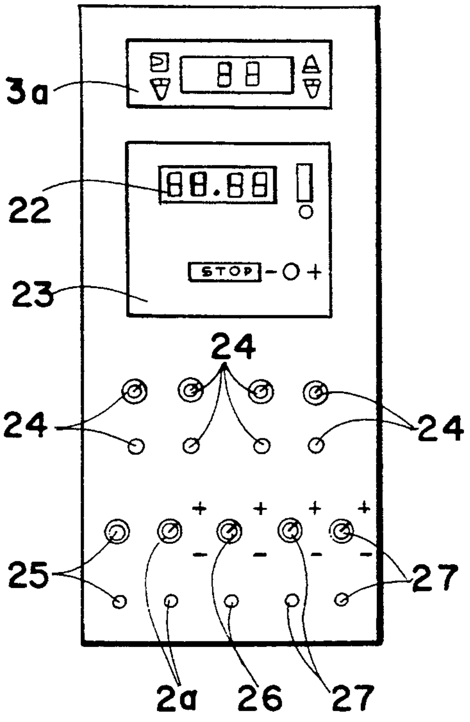
FIG. 5 is a schematic view of a functions management/control panel.

FIG. 5 shows a control panel having a digital thermometer 3*a*, a digital time counter 22, a stop warning display 23, valve control switches 24, each with its relevant LED, a main circuit breaker 25, a steam control variometer 2*a*, an air control variometer 26 and ozone control variometer 27. All of these control elements are provided with a relevant operations-signalling LED.

In order to increase the efficiency of the bell-shaped headpiece 19, a "T"-fitting can be installed on the steam outlet from the boiler, i.e, on the initial portion of duct 6, with all downstream components, as disclosed hereinabove, being duplicated, and with both streams of treatment mixture produced in that way being combined in the end portion of duct 6, before entering the headpiece 19.

The whole as disclosed and illustrated hereinabove, with possibility of modifications and improvements being supplied within the scope of the basic principle of the invention, with the latter remaining unchanged.

We claim:

1. An apparatus for controllably treating hair of a user with a nebulized mixture of air, steam and ozone, the apparatus comprising:

a boiler (1) containing water to produce steam and condensate;

heating means (2) for heating the water;

temperature detection means (3) for detecting the temperature of the water;

control means (2*a*) for controlling the temperature of the water;

compressed air production means (15) for providing compressed air;

an ozone generator (14) for providing ozone comprising a pair of capacitors (14*a* ) operatively connected to a pair of generator bulbs (14*b*) and a wrapping net surrounding the capacitors and the bulbs, the wrapping net having mesh openings less than approximately 0.5 $mm^2$, the wrapping net also having a cross-section surface area ranging approximately from 0.1 to 0.3 $mm^2$;

duct means (6, 7, 8*a*, 9*a*, 10*a*, 11, 11*a*, 18) communicating with the boiler, the compressed air generator and the ozone generator for distributing steam, compressed air, ozone and condensate;

mixing means (8, 13) communicating with the duct means for mixing the compressed air with ozone to produce ozonized air and for mixing the ozonized air with steam, the ozonized air with steam defining a treatment mixture; and a headpiece (19) for covering the hair of the user and communicating with the duct means for receiving the treatment mixture.

2. The apparatus according to claim 1, including display means (3*a*) for displaying the temperature of the water.

3. The apparatus according to claim 1, including a supplementary water tank (4) having a water inlet pipe (4*a*) communicating with the boiler for supplying water to the boiler.

4. The apparatus according to claim 3, including a water level regulation float (4*b*) on the inlet pipe.

5. The apparatus according to claim 1, where the duct means comprises solenoid valve means (5, 10).

6. The apparatus according to claim 5, wherein the duct means further comprises a non-return valve (12).

7. The apparatus according to claim 6, wherein the duct means further comprises a condensate discharge chamber (9).

8. The apparatus according to claim 1, including control switch means (24) for controlling the duct means.

* * * * *